United States Patent
Pettit et al.

(10) Patent No.: US 7,789,513 B2
(45) Date of Patent: Sep. 7, 2010

(54) ADAPTIVE WAVEFRONT MODULATION SYSTEM AND METHOD FOR REFRACTIVE LASER SURGERY

(75) Inventors: George H. Pettit, Maitland, FL (US); John A. Campin, Orlando, FL (US)

(73) Assignee: Alcon Refractivehorizons, Inc., Fort Worth, TX (US)

( * ) Notice: Subject to any disclaimer, the term of this patent is extended or adjusted under 35 U.S.C. 154(b) by 156 days.

(21) Appl. No.: 12/106,439

(22) Filed: Apr. 21, 2008

(65) Prior Publication Data

US 2008/0259279 A1 Oct. 23, 2008

Related U.S. Application Data

(60) Provisional application No. 60/913,035, filed on Apr. 20, 2007.

(51) Int. Cl.
*A61B 3/00* (2006.01)
*A61B 3/10* (2006.01)

(52) U.S. Cl. .................................. 351/246; 351/212

(58) Field of Classification Search ......... 351/200–246; 606/4–5
See application file for complete search history.

(56) References Cited

U.S. PATENT DOCUMENTS

| | | | | |
|---|---|---|---|---|
| 6,270,221 | B1 | 8/2001 | Liang et al. | 351/221 |
| 6,682,196 | B2 * | 1/2004 | Sheets et al. | 351/246 |
| 6,698,889 | B2 * | 3/2004 | Pettit et al. | 351/246 |
| 7,226,443 | B1 * | 6/2007 | Campin et al. | 606/5 |
| 7,237,898 | B1 | 7/2007 | Hohla et al. | 351/246 |
| 2003/0086063 | A1 | 5/2003 | Williams et al. | 351/221 |
| 2004/0070730 | A1 | 4/2004 | Mihashi et al. | 351/221 |
| 2006/0235369 | A1 | 10/2006 | MacRae et al. | 606/4 |
| 2007/0008491 | A1 | 1/2007 | Polland et al. | 351/212 |
| 2007/0273828 | A1 | 11/2007 | Polland et al. | 351/204 |
| 2008/0306573 | A1 * | 12/2008 | Campin et al. | 607/89 |

FOREIGN PATENT DOCUMENTS

| | | |
|---|---|---|
| DE | 10333813 A1 | 2/2005 |
| EP | 1364612 A1 | 11/2003 |
| WO | WO9927334 | 6/1999 |
| WO | 01/28410 A1 | 4/2001 |
| WO | 2005/015290 A2 | 2/2005 |
| WO | 2006/110922 A2 | 10/2006 |

* cited by examiner

*Primary Examiner*—Mohammed Hasan
(74) *Attorney, Agent, or Firm*—Armando Pastrana, Jr.

(57) ABSTRACT

A method for improving an accuracy of a prescription for laser-ablation corneal treatment includes the step of receiving a set of raw data comprising Hartmann-Shack image data obtained from a plurality of aberrometer measurements of a patient eye. The Hartmann-Shack data can include, for example, a dot pattern image for each measurement. A set of reconstructed wavefront data calculated from the set of raw data for the plurality of aberrometer measurements is also received. Data on a selected component of the set of raw data and in the set of reconstructed wavefront data are compared. If the selected component data differ more than a predetermined amount between the raw data and the reconstructed wavefront data, the raw data can be further manipulated prior to undertaking laser ablation. In addition, these data are removed from consideration for inclusion in the database of treatment outcomes.

12 Claims, 4 Drawing Sheets though typically clinicians are not skilled in the analytic interpretations of these mathematical parameters. In addition, at present there is no known convenient method for a surgeon to modify a wavefront-based prescription prior to a procedure such as laser surgery.

ADAPTIVE WAVEFRONT MODULATION SYSTEM AND METHOD FOR REFRACTIVE LASER SURGERY

CROSS-REFERENCE TO RELATED APPLICATIONS

This application claims priority under 35 U.S.C. §119 to U.S. Provisional Patent Application No. 60/913,035 filed Apr. 20, 2007 the entire contents of which are incorporated herein by reference.

BACKGROUND OF THE INVENTION

1. Field of the Invention

The present invention relates to systems and methods for performing refractive laser surgery on the eye, and, more particularly, to such systems and methods that process data for use as input for a system that adaptively modulates sensed data on the basis of data from prior procedures.

2. Description of Related Art

In a particular treatment system for calculating a laser ablation treatment profile for an eye to improve vision, a plurality of Hartmann-Shack measurements are collected, and the image of the resulting dot pattern is enhanced. The position of each dot is measured, and wavefront slope data are calculated from the dot centroids. The original wavefront is then reconstructed mathematically.

The results of these calculations for each of the plurality of measurements are then compared, and any "outliers" are removed. The remaining reconstructed wavefronts are combined to form a composite result, which is in turn used to define an ablation treatment profile. In addition, a "classical" prescription can be calculated from the composite result, which can be compared with the results of a phoropter measurement.

A clinician typically modifies the prescription entered into the treatment system. Such modifications are based upon prior experience with outcomes achieved with that particular treatment system, and also upon experience with particular patient populations derived from, for example, demographic data. For example, a surgeon might enter a 2-diopter myopic treatment prescription for a patient diagnosed with 3 diopters of myopia if analysis of previous outcomes indicates a 50% overcorrection using this system for patients of a particular category. Such an empirical alteration of entered treatment parameters based upon previous experience is referred to as a nomogram adjustment. Nomograms are considered essential by the ophthalmic community because different clinicians employ different surgical techniques, operate under different environmental conditions, have distinct patient demographics, etc.

Conventional surgery involves a limited number of well-defined treatment parameters, principally spherical error, astigmatic error, astigmatic axis, optical zone size, and blend zone size. Thus it is relatively straightforward for a surgeon to develop nomogram formulas based on conventional clinical examinations before and after surgical procedures. In contrast, wavefront-guided customized treatments, such as that disclosed in commonly owned U.S. Pat. No. 6,270,221 B1, the disclosure of which is incorporated herein by reference, involve complex a mathematical description of the pre-operative aberration profile, which is transferred electronically to the treatment system.

Although such a precise wavefront description can in theory be modified empirically to yield a better outcome, typically clinicians are not skilled in the analytic interpreta- In currently used wavefront-based treatments, the raw wavefront data are modulated to generate a treatment profile in order to account for an apparent radial dependence in the effectiveness of ablative treatment on the corneal tissue. This, however, is currently applied identically in all treatments.

The inventors of the present application have previously disclosed a system and method for creating a nomogram for adaptively modulating sensed wavefront data based upon prior treatment outcomes (U.S. Pat. No. 6,698,889, which is commonly owned herewith, and the contents of which are incorporated hereinto by reference).

Aberrometers known in the art can calculate and display on screen an effective clinical prescription from a wavefront profile. In most cases the wavefront-derived prescription is in good agreement with independent sphere/cylinder/axis data obtained via classical refraction. However, in some case the wavefront values are significantly different, and are perceived as incorrect. This most commonly occurs in post-operative cases, that is, examinations performed after the patient has had laser vision correction surgery. At present there exists no system to assess confidence in the final reported refraction estimate.

A dubious refraction reported by an aberrometer can erode physician confidence in the aberrometer's general performance. In addition, such a result can be indicative of a problem with the measurement, which could, for example, be remedied with a repeat measurement. An example of such an eventuality is if the patient's tear film is breaking up due to infrequent blinking. Furthermore, such questionable data should not be included in any automatic trend analysis as taught in the '889 patent for nomogram optimization.

There yet remains a need for refining the data that are used as input for the system and method described in the '889 patent and similar systems, and also for alerting a clinician if a calculated prescription is suboptimal.

SUMMARY OF THE INVENTION

The present invention is directed to a system and method for refining a prescription for laser-ablation corneal treatment, and for optimizing a data set that is used for creating empirically derived nomograms from a database of treatment outcomes on a plurality of previously treated patients. The database contains, for each previously treated patient, at least one classification element and also comprises a preoperative wavefront-determined correction prescription and a postoperative visual profile. A difference between the preoperative correction prescription and the postoperative visual profile represents an over- or undercorrection resulting from the surgery.

A method for improving an accuracy of a prescription for laser-ablation corneal treatment comprises the steps of receiving a set of raw data comprising Hartmann-Shack image data obtained from a plurality of aberrometer measurements of a patient eye. The Hartmann-Shack data can comprise, for example, a dot pattern image for each measurement. A set of reconstructed wavefront data calculated from the set of raw data for the plurality of aberrometer measurements is also received. Typically the reconstructed wavefront data are obtained as outlined above.

Data on a selected component of the set of raw data and in the set of reconstructed wavefront data are compared. If the selected component data differ more than a predetermined amount between the raw data and the reconstructed wavefront data, the raw data can be further manipulated prior to undertaking laser ablation, or the laser ablation may be recommended not to occur. In addition, these data are removed from consideration for inclusion in the database of treatment outcomes.

Another aspect of the present invention includes a software package resident on a computer-readable medium for performing the calculational steps outlined above.

The present invention is believed to represent a first method of filtering wavefront data to identify measurement data yielding suspect computed refractions. The invention thus provides a mechanism for ensuring that prescriptions reported by the aberrometer device are as accurate as possible. The invention then gives the operator confidence in the instrument, alerts the operator in cases in which the wavefront examination may be suboptimal, and removes spurious data from a database used to compute treatment trends.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 1:
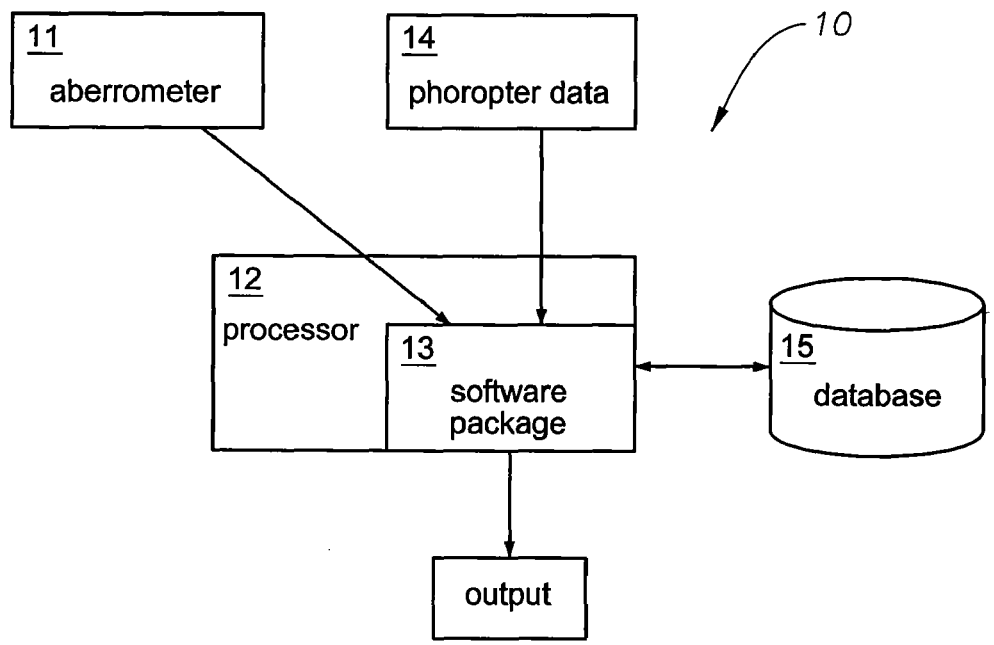
FIG. 1 is an exemplary system schematic for the present invention.

A description of the preferred embodiments of the present invention will now be presented with reference to FIGS. 1-4.

The system 10 (FIG. 1) and method 100 (FIGS. 2A, 2B) of the present invention are directed, in a particular embodiment, to improving an accuracy of a prescription for laser-ablation corneal treatment. In a preferred embodiment a plurality of, for example, five, Hartmann-Shack measurements will have been made using a wavefront determination apparatus, including an aberrometer 11 and a processor 12 having software 13 resident thereon. The wavefront determination aberration is used for a patient to provide a set of raw data on the patient's eye (block 101). From these raw data, for each of the measurements, are calculated dot locations, dot centroid locations, wavefront slope data from the dot centroids, and a mathematical reconstruction of the wavefronts, for example, using Zernike polynomials to a predetermined order (block 102).

The reconstruction data contain implied dot and dot centroid locations, and a calculated center of the wavefront map. Typically, in a particular embodiment wherein five measurements are made, the wavefront data for the five measurements are compared statistically, and the two most significant outliers are removed prior to forming the composite result, which includes a high-fidelity representation, or map, of the aberration content of the eye (block 103). The composite result is used to define a laser ablation treatment profile (block 104) and a "classical" (diopter) prescription (block 105).

The system also receives phoropter 14 data measured on the patient's eye (block 106). The classical prescription can be compared with phoropter data in order to determine agreement there between. If the agreement is within a predetermined range (block 107), the ablation treatment can proceed (block 108); if not, the physician may decide to undertake further study on the patient (block 109). In a particular embodiment, it is desired to achieve a 95% confidence interval of 0.6 D for both pre- and post-operative measurements.

At least one of a plurality of methods (block 110) can be employed to flag data sets that may indicate a suboptimal result, which could reduce confidence in the treatment prescription, and also to filter out data sets from subsequent inclusion in a database 15 of treatment outcomes that is used for calculating a nomogram.

A first method includes processing the raw Hartmann-Shack image. Statistics are calculated as to the variations of individual dots in the Hartmann-Shack image (block 111), as well as deviations between the measured dot centroids and the centroids implied by the wavefront reconstruction (block 112). Particular variations in the Hartmann-Shack dot pattern may be indicative of tear film break-up or other physiological anomaly, which would compromise the wavefront calculation. Significant deviations between the measured and implied centroid locations (block 113) may indicate insufficient Zernike orders in the reconstruction, which also could lead to incorrect treatment estimation. Therefore, one option would be to recalculate the wavefront reconstruction data using higher-order Zernike polynomials, for example (block 114). In addition, these data will not be included in the nomogram database 15 (block 115). A close match between the data sets will typically give the operator confidence in the measurement, treatment can proceed (block 116), and the data are included in the nomogram database (block 117).

A second method (block 110) includes calculating variations between multiple wavefront measurements. If the five individual measurements yield substantially varying computed refractions (block 118), the patient may not have fixated consistently during the examination, and the examination may be repeated (block 119). Again, these data will not be included in the nomogram database 15 (block 115). If the variations are acceptable (block 118), treatment can proceed (block 116), and the data are included in the nomogram database (block 117).

Figure 3:
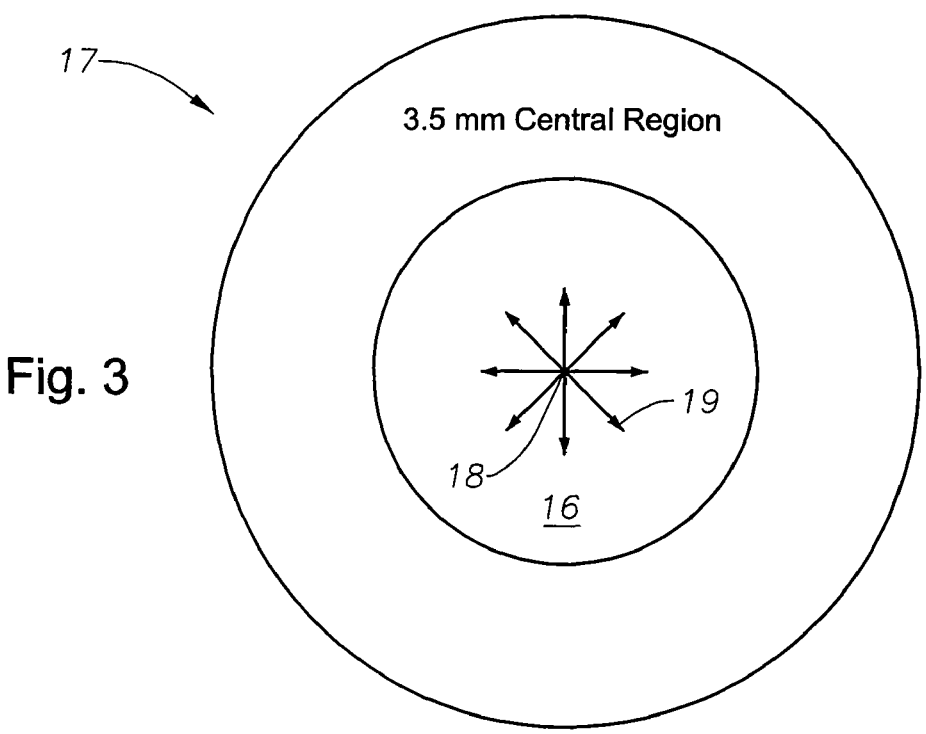
FIG. 3 illustrates an exemplary wavefront map for calculating the effect of decentration on calculated treatment parameters.
Figure 2A:
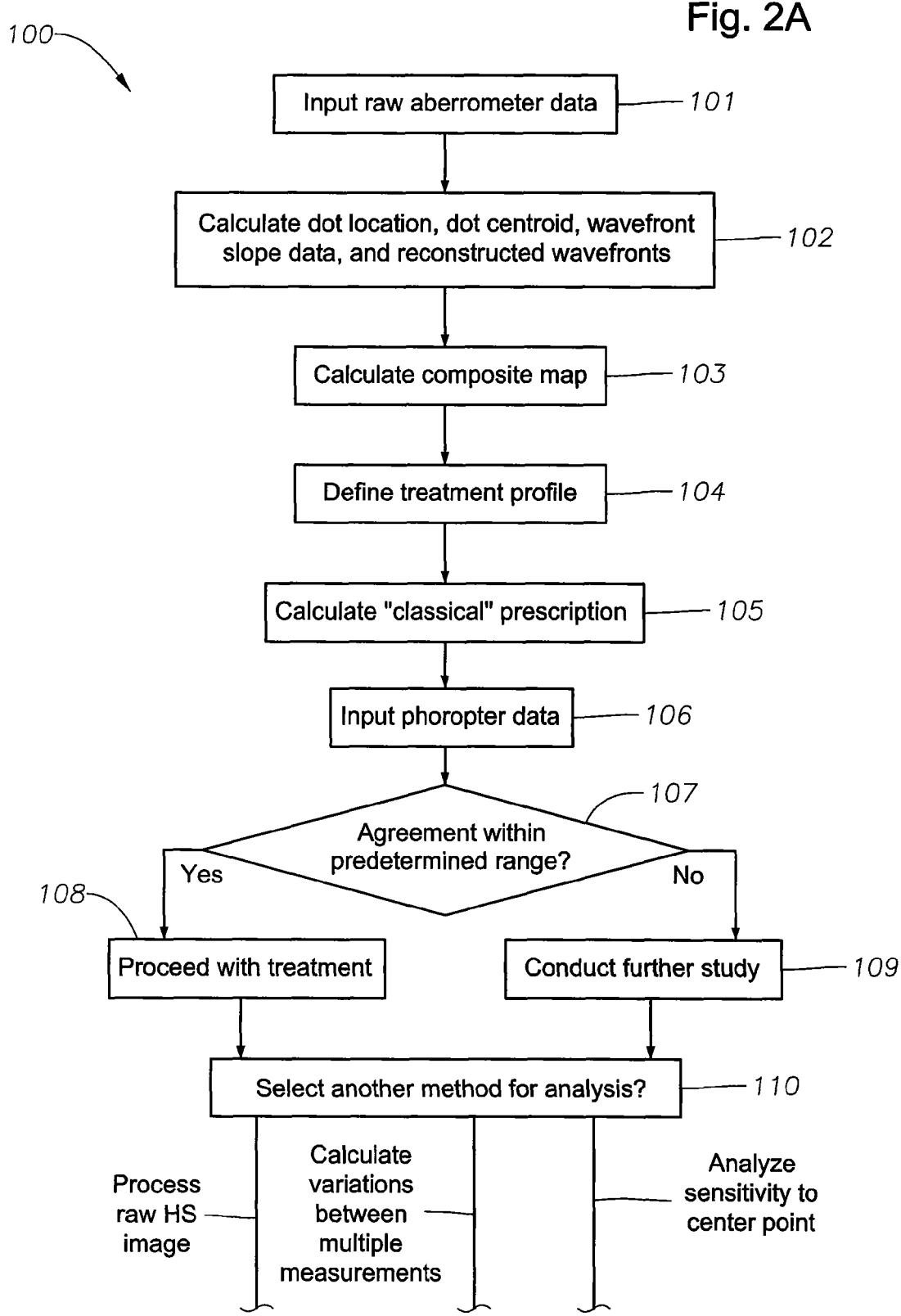
FIGS. 2A, 2B is a flow chart of a method for improving an accuracy of a prescription for laser-ablation corneal treatment.
Figure 2B:
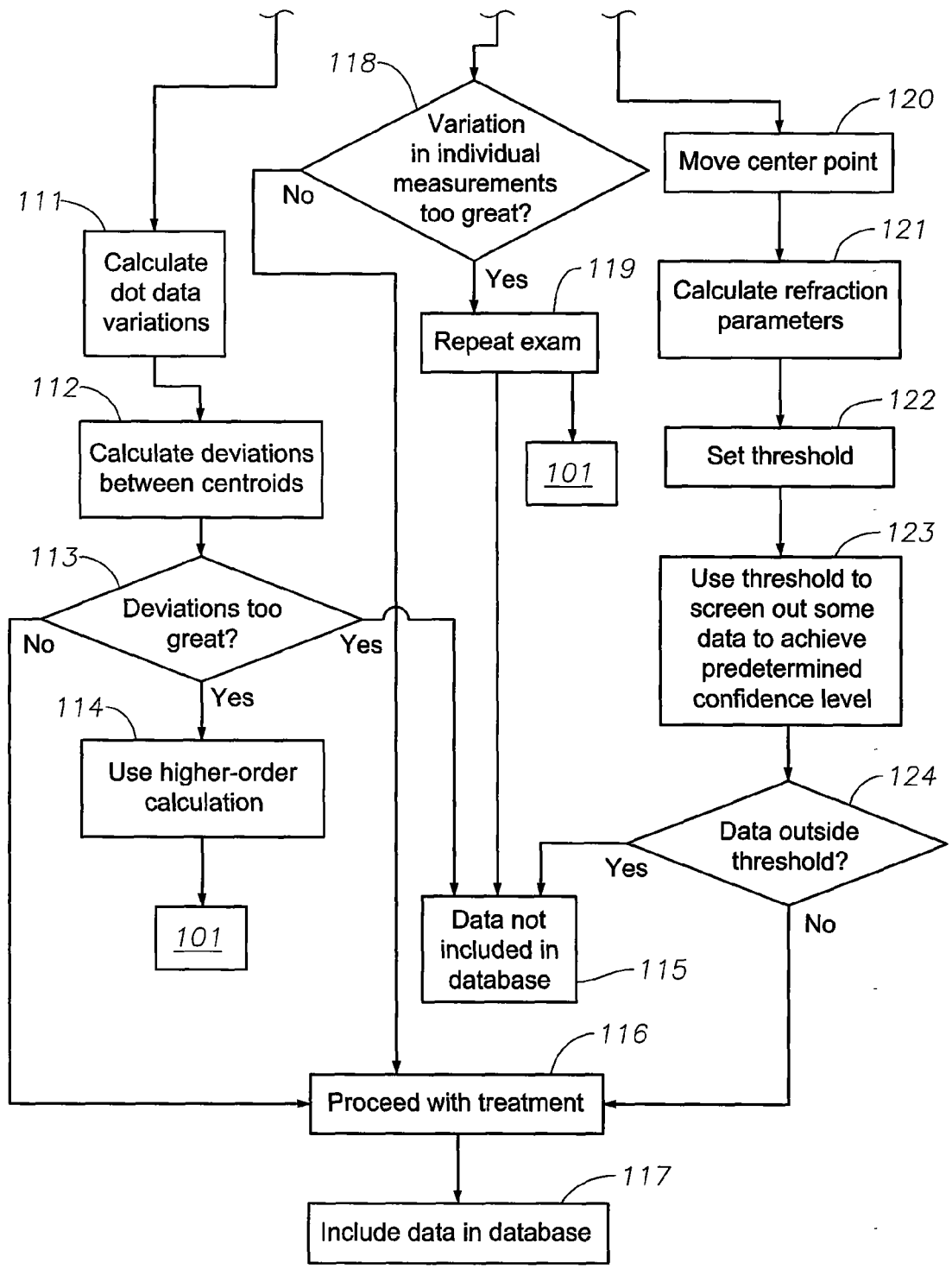

A third method (block 110) comprises testing the sensitivity of the calculated prescription to the choice of mathematical reference center of the wavefront map (FIG. 3). In a particular embodiment, the reported treatment prescription will have been calculated from the second-order aberrations over a center portion 16, for example, a 3.5-mm circle, of the wavefront reconstruction, which can comprise, for example, a 6.5-mm wavefront map 17. The software 13 is then used to "decenter" the image, for example, by moving the center position 18 that had previously been calculated and used to form the wavefront data, in a plurality of radial directions 19 (block 120). In an exemplary embodiment, a displacement of 100 μm is made in eight radial directions.

For each of the decentrations, the standard deviation in the calculated refraction parameters, which can include defocus, cardinal astigmatism, and oblique astigmatism, is calculated (block 121). This gives an indication of refraction sensitivity to the choice of origin 18.

Figure 4:
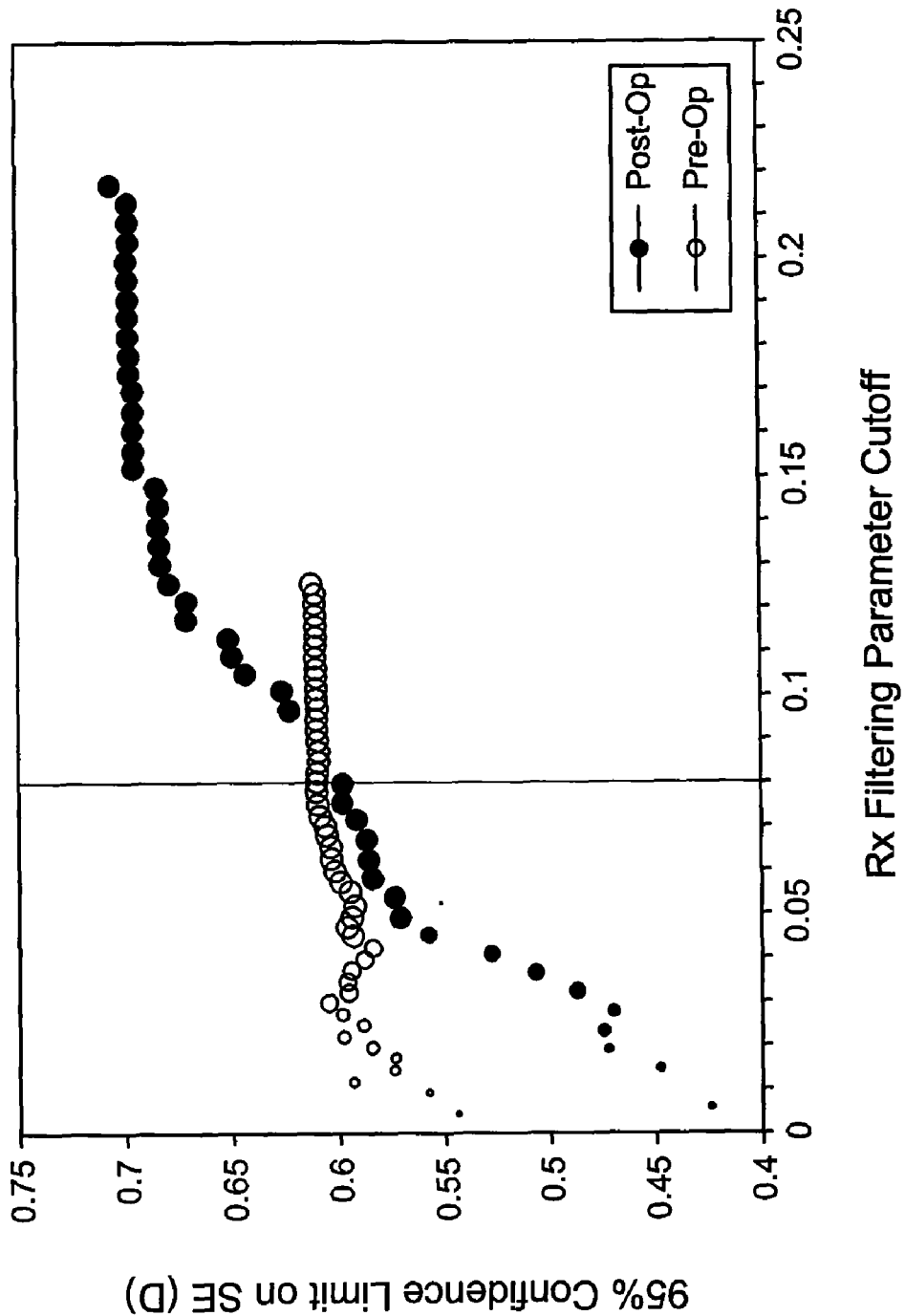
FIG. 4 is a graph of a 95% confidence limit on standard error, in diopters, versus a treatment filtering parameter cutoff.

In FIG. 4 is plotted the performance of this filtering method on large populations of pre- and post-operative eyes. For this plot, data from >740 eyes, approximately evenly distributed between myopes and hyperopes, were used. The horizontal axis indicates the allowable cutoff in the filter parameter. Cases for which the parameter is greater than the cutoff are rejected. The vertical axis indicates the 95% confidence interval in the wavefront/phoropter difference for the filtered population. The area of each dot indicates the relative fraction of all eyes included in the filtered data set.

For this study, using a threshold (block 122) that screens out ~7% of all post-operative eye data and only ~1% of pre-operative eye data, the 95% confidence interval is reduced to 0.6 D for both groups (block 123), which is a predetermined maximum value for this parameter. Data for a patient having a wavefront/phoropter difference greater than this predetermined level (block 124) will not be included in the nomogram database 15 (block 115). If the variations are acceptable (block 124), treatment can proceed (block 117), and the data are included in the nomogram database (block 117).

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the system and method illustrated and described herein are by way of example, and the scope of the invention is not limited to the exact details disclosed herein.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for improving an accuracy of a prescription for laser-ablation corneal treatment comprising the steps of:
   receiving a set of raw data comprising Hartmann-Shack image data obtained from a plurality of aberrometer measurements of a patient eye;
   receiving a set of reconstructed wavefront data calculated from the set of raw data for the plurality of aberrometer measurements;
   comparing data on a selected component of the set of raw data and in the set of reconstructed wavefront data;
   if the selected component data differ more than a predetermined amount between the raw data and the reconstructed wavefront data, further manipulating the raw data prior to undertaking laser ablation;
   receiving a diopter prescription calculated from the raw data for each of the plurality of aberrometer measurements, the reconstructed wavefront data including the diopter prescriptions, wherein the selected component data comprise the diopter prescriptions; and
   if a deviation between the diopter prescriptions is greater than a predetermined amount, receiving new sets of raw data and reconstructed wavefront data collected with additional aberrometer measurements.

2. The method recited in claim 1, wherein the Hartmann-Shack image data comprise position and centroid data on a plurality of dots comprising the Hartmann-Shack image, and wherein the selected component comprises at least one of the dot position and the dot centroid data.

3. The method recited in claim 1, wherein the reconstructed wavefront data receiving step comprises receiving wavefront data reconstructed with the use of Zernike polynomials up to a predetermined order, and wherein the further manipulating step comprises reconstructing the raw data using Zernike polynomials up to an order greater than the predetermined order.

4. The method recited in claim 1, further comprising the step of, if the selected component data of the raw data and the reconstructed wavefront data differ by less than the predetermined amount, including the raw data and the reconstructed wavefront data in a database of treatment outcomes on a plurality of previously treated patients, each treated patient outcome having associated therewith at least one classification element and comprising a preoperative wavefront-determined correction prescription and a postoperative visual profile, the database for creating a nomogram for adaptively modulating sensed wavefront data based upon data therein.

5. A method for improving an accuracy of a prescription for laser-ablation corneal treatment comprising the steps of:
   receiving a set of raw data comprising Hartmann-Shack image data obtained from a plurality of aberrometer measurements of a patient eye;
   receiving a set of reconstructed wavefront data calculated from the set of raw data for the plurality of aberrometer measurements;
   comparing data on a selected component of the set of raw data and in the set of reconstructed wavefront data;
   if the selected component data differ more than a predetermined amount between the raw data and the reconstructed wavefront data, further manipulating the raw data prior to undertaking laser ablation;
   receiving a prescription for the eye determined with the use of a phoropter and a diopter prescription calculated from the reconstructed wavefront data; and
   if the phoropter-determined prescription and the calculated diopter prescription differ by more than a predetermined amount, receiving new sets of raw data and reconstructed wavefront data collected with additional aberrometer measurements.

6. A method for improving an accuracy of a prescription for laser-ablation corneal treatment comprising the steps of:
   receiving a set of raw data comprising Hartmann-Shack image data obtained from a plurality of aberrometer measurements of a patient eye;
   receiving a set of reconstructed wavefront data calculated from the set of raw data for the plurality of aberrometer measurements;
   comparing data on a selected component of the set of raw data and in the set of reconstructed wavefront data; and
   if the selected component data differ more than a predetermined amount between the raw data and the reconstructed wavefront data, further manipulating the raw data prior to undertaking laser ablation;
   wherein the reconstructed wavefront data include an initial calculated position of a center thereof, and further comprising the steps of:
   moving a center position by a predetermined amount in a radial direction from the initial calculated position to a radially displaced position;
   calculating from the raw data an adjusted set of refraction parameters using the radially displaced position for the center position;

repeating the moving and calculating steps a plurality of times for different radial directions to yield a plurality of adjusted sets of refraction parameters;

comparing the plurality of adjusted sets of refraction parameters; and if at least one of the refraction parameters varies with radial direction movement more than a predetermined amount, performing further study on the eye prior to proceeding with laser ablation treatment.

7. A system for improving an accuracy of a prescription for laser-ablation corneal treatment comprising:

a processor;

a software package resident on the processor comprising software code segments for:

receiving a set of raw data comprising Hartmann-Shack image data obtained from a plurality of aberrometer measurements of a patient eye;

receiving a set of reconstructed wavefront data calculated from the set of raw data for the plurality of aberrometer measurements;

comparing data on a selected component of the set of raw data and in the set of reconstructed wavefront data; and if the selected component data differ more than a predetermined amount between the raw data and the reconstructed wavefront data, outputting a need for further manipulation of the raw data prior to undertaking laser ablation;

wherein the software package further comprises a software code segment for receiving a diopter prescription calculated from the raw data for each of the plurality of aberrometer measurements, the reconstructed wavefront data including the diopter prescriptions, wherein the selected component data comprise the diopter prescriptions, and further comprising a software code segment for, if a deviation between the diopter prescriptions is greater than a predetermined amount, receiving new sets of raw data and reconstructed wavefront data collected with additional aberrometer measurements.

8. The system recited in claim 7, wherein the Hartmann-Shack image data comprise position and centroid data on a plurality of dots comprising the Hartmann-Shack image, and wherein the selected component comprises at least one of the dot position and the dot centroid data.

9. The system recited in claim 7, wherein the reconstructed wavefront data receiving code segment comprises a code segment for receiving wavefront data reconstructed with the use of Zernike polynomials up to a predetermined order, and wherein the further manipulation comprises reconstructing the raw data using Zernike polynomials up to an order greater than the predetermined order.

10. The system recited in claim 7, wherein the software package further comprises code segments for receiving a prescription for the eye determined with the use of a phoropter and a diopter prescription calculated from the reconstructed wavefront data, and for, if the phoropter-determined prescription and the calculated diopter prescription differ by more than a predetermined amount, receiving new sets of raw data and reconstructed wavefront data collected with additional aberrometer measurements.

11. A system for improving an accuracy of a prescription for laser-ablation corneal treatment comprising:

a processor;

software package resident on the processor comprising software code segments for:

receiving a set of raw data comprising Hartmann-Shack image data obtained from a plurality of aberrometer measurements of a patient eye;

receiving a set of reconstructed wavefront data calculated from the set of raw data for the plurality of aberrometer measurements;

comparing data on a selected component of the set of raw data and in the set of reconstructed wavefront data; and if the selected component data differ more than a predetermined amount between the raw data and the reconstructed wavefront data, outputting a need for further manipulation of the raw data prior to undertaking laser ablation; and a database of treatment outcomes on a plurality of previously treated patients in signal communication with the processor, each treated patient outcome having associated therewith at least one classification element and comprising a preoperative wavefront-determined correction prescription and a postoperative visual profile, the database for creating a nomogram for adaptively modulating sensed wavefront data based upon data therein, and wherein the software package further comprises a software code segment for, if the selected component data of the raw data and the reconstructed wavefront data differ by less than the predetermined amount, transmitting the raw data and the reconstructed wavefront data to the database.

12. A system for improving an accuracy of a prescription for laser-ablation corneal treatment comprising:

a processor;

a software package resident on the processor comprising software code segments for:

receiving a set of raw data comprising Hartmann-Shack image data obtained from a plurality of aberrometer measurements of a patient eye;

receiving a set of reconstructed wavefront data calculated from the set of raw data for the plurality of aberrometer measurements;

comparing data on a selected component of the set of raw data and in the set of reconstructed wavefront data; and if the selected component data differ more than a predetermined amount between the raw data and the reconstructed wavefront data, outputting a need for further manipulation of the raw data prior to undertaking laser ablation;

wherein the reconstructed wavefront data include an initial calculated position of a center thereof, and wherein the software package further comprises code segments for:

moving a center position by a predetermined amount in a radial direction from the initial calculated position to a radially displaced position;

calculating from the raw data an adjusted set of refraction parameters using the radially displaced position for the center position;

repeating the moving and calculating steps a plurality of times for different radial directions to yield a plurality of adjusted sets of refraction parameters;

comparing the plurality of adjusted sets of refraction parameters; and if at least one of the refraction parameters varies with radial direction movement more than a predetermined amount, outputting a suggestion to perform further study on the eye prior to proceeding with laser ablation treatment.

* * * * *